(12) United States Patent
Mallia et al.

(10) Patent No.: US 7,745,153 B2
(45) Date of Patent: Jun. 29, 2010

(54) PYROCATECHOL VIOLET-METAL PROTEIN ASSAY

(75) Inventors: A. Krishna Mallia, Rockford, IL (US); Babu S. Antharavally, Caledonia, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 361 days.

(21) Appl. No.: 12/027,065

(22) Filed: Feb. 6, 2008

(65) Prior Publication Data

US 2009/0197348 A1 Aug. 6, 2009

(51) Int. Cl.
*G01N 33/53* (2006.01)

(52) U.S. Cl. .......................... 435/7.21; 435/2; 435/7.1; 436/501; 436/518; 436/522; 422/50; 422/61; 530/300; 530/350

(58) Field of Classification Search ........................ None
See application file for complete search history.

(56) References Cited

U.S. PATENT DOCUMENTS 5,360,899 A 11/1994 Nussstein

FOREIGN PATENT DOCUMENTS

| EP | 0312249 | 4/1989 |
|---|---|---|
| EP | 0952451 | 10/1999 |
| EP | 1560027 | 8/2005 |
| WO | WO 2007/111847 | 10/2007 |
| WO | WO 2007/125372 | 11/2007 |

OTHER PUBLICATIONS

Gornall et al., J. Biol. Chem. 177: 751 (1949).
Lowry et al., J. Biol. Chem. 193: 265 (1951).
Smith et al., Anal. Biochem. 150: 76 (1985).
Bradford, Anal. Biochem. 72: 248 (1976).
Stoscheck, Anal. Biochem. 160: 301 (1987).
Okutani et al., Anal. Sci. 14: 621 (1998).
Watanabe et al., Clin. Chem. 32: 1551 (1986).
Fujita et al., Chem. Pharm. Bull. 32: 4161 (1984).
European Search Report, dated May 19, 2009, 7 pages.
Delacour H, et al., Interférences médicamenteuses sur le dosage des protéin urinaires avec les plaques Upro Vitros® au violet de pyrocatéchol. Annales de Biologie Clinique, vol. 61, No. 6, 2003, pp. 709-712.
Arnold, Thomas, and Linke, Dirk, Phase separation in the isolation and purification of membrane proteins. *BioTechniques* 43(4): 427 (Oct. 2007).
Gombotz, et al. The stabilization of a human IgM monoclonal antibody with poly(vinylpyrrolidone). *Pharmaceutical Research*, vol. 11(5): 624 (1994).
Li, et al. Immobilized β-cyclodextrin polymer coupled to agarose gel properly refolding recombinant *Staphylococcus aureus* elongation factor-G in combination with detergent micelle. *Protein Expression & Purification* 45:72-79 (2006).
Okubo et al., Inclusion process of ionic detergents with cyclodextrins as studied by the conductance stopped-flow method. *J. Phys. Chem.* 93, 3721-3723 (1989).
Polyvinylpyrrolidone, Wikipedia; http://en.wikipedia.org/wiki/Polyvinylpyrrolidone.
Thermo Scientific Product Literature for Pierce 660 nm Protein Assay, Thermo Fisher Scientific Inc. (2008).

*Primary Examiner*—Lisa V Cook
(74) *Attorney, Agent, or Firm*—Thompson Hine LLP

(57) ABSTRACT

A method for protein determination utilizing a pyrocatechol violet-metal complex, a composition used in the protein determination assay, and a kit.

32 Claims, 5 Drawing Sheets

PYROCATECHOL VIOLET-METAL PROTEIN ASSAY

TECHNICAL FIELD

A composition, method, and kit for use in a protein determination assay.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
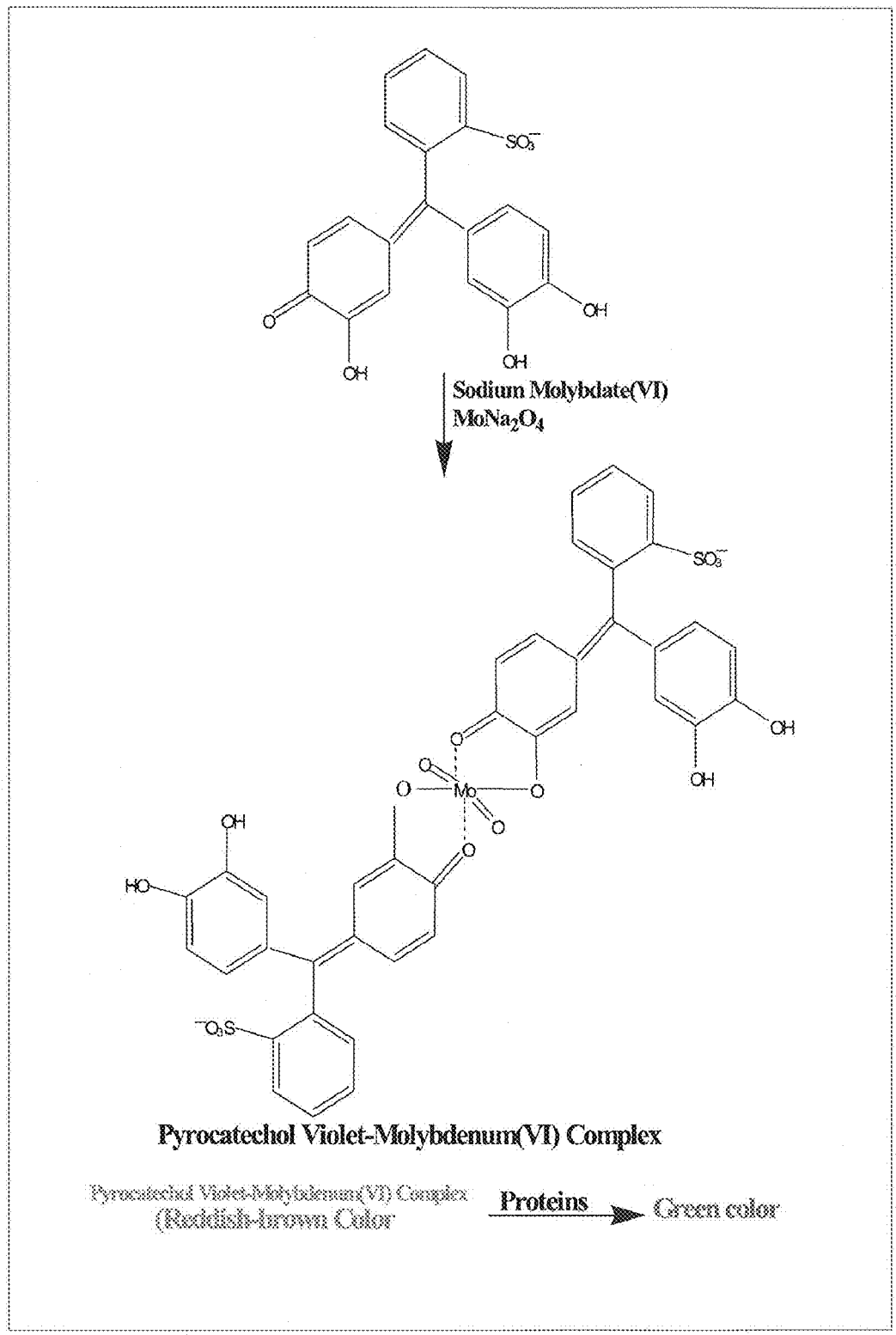
FIG. 1 shows formation of the pyrocatechol violet-metal (PVM) complex.

A composition, a method, and a kit for a colorimetric protein assay. The method is rapid, sensitive, and has reduced interference from detergents, reducing agents and other common reagents compared to commercial methods. It has an expanded linear working range compared to commercial methods. It exhibits minimal protein-to-protein variation.

In one embodiment, a protein assay reagent composition comprises polyhydroxybenzenesulfonephthalein- or polyhydroxybenzenephthalein-type dyes such as pyrocatechol violet (PCV) along with a metal. In one embodiment, the metal can be molybdenum, tungsten, bismuth, thorium, uranium, vanadium, or copper, or combinations thereof. In one embodiment, the metal is molybdenum. In embodiments, the metal is present as a sodium, potassium, lithium, or ammonium salt. In one embodiment, the metal is sodium molybdate or sodium tungstate. Additional components of the composition include polyvinyl alcohol, optionally methanol, a buffer, polyvinyl pyrrolidone, and at least one of a chelating agent, α-cyclodextrin or sodium benzoate.

In another embodiment, a method of determining protein concentration in a biological sample comprises combining the sample with a protein assay reagent composition comprising pyrocatechol violet and a metal, incubating the mixture of the sample and the protein assay reagent composition until a colored complex is formed, measuring the absorbance of the colored complex, and determining the protein concentration in the sample by comparing the measured absorbance with the absorbance obtained from samples containing known concentrations of protein (standards). In one embodiment, the metal can be molybdenum, tungsten, bismuth, thorium, uranium, vanadium, or copper, or combinations thereof. In one embodiment, the metal is molybdenum. In embodiments, the metal is present as a sodium, potassium, lithium, or ammonium salt. In one embodiment, the metal is sodium molybdate or sodium tungstate.

In another embodiment, a kit for determining protein concentration comprises a protein assay reagent composition comprising pyrocatechol violet and a metal, at least one protein in a known concentration, and instructions for determining protein concentration using the kit components. In one embodiment, the metal can be molybdenum, tungsten, bismuth, thorium, uranium, vanadium, or copper, or combinations thereof. In one embodiment, the metal is molybdenum. In embodiments, the metal is present as a sodium, potassium, lithium, or ammonium salt. In one embodiment, the metal is sodium molybdate or sodium tungstate.

Accurate protein quantitation in a sample is required to study many biochemical processes. For determining relative protein concentration in solution, colorimetric or chromogenic methods are widely used because of their simplicity and speed. Commercially available methods for the colorimetric determination of protein concentration in solution include the Biuret method (Gornall et al. J. Biol. Chem. 177: 751, 1949), the Lowry method (Lowry et al. J. Biol. Chem. 193: 265, 1951), the bicinchoninic acid (BCA) method (Smith et al. Anal. Biochem. 150: 76, 1985), Coomassie Blue G-250 dye-binding method (Bradford, Anal. Biochem. 72: 248, 1976), and colloidal gold protein method (Stoscheck, Anal. Biochem. 160: 301, 1987).

The Biuret method is based on protein forming a complex with cupric ions. Under alkaline conditions, copper(II) ion is bound to peptide nitrogen of proteins and peptides to produce a purple color with an absorption maximum at 550 nm. The sensitivity is 1 mg protein/ml to 6 mg protein/ml. The Biuret method is a relatively insensitive protein determination method compared to other commercial methods of colorimetric protein determination.

The Lowry method is a modified Biuret reaction in which peptide bonds react with copper(II) ions under alkaline conditions followed by the Folin-Ciocalteau phosphomolybdic-phosphotungstic acid reduction to heteropolymolybdenum blue by the copper-catalyzed oxidation of aromatic amino acids. The absorption maximum of the product is 750 nm. The Lowry method is more sensitive than the Biuret method with a linear sensitivity of 0.1 mg protein/ml to 1.5 mg protein/ml of bovine serum albumin (BSA). Certain amino acids, detergents, lipids, sugars, and nucleic acids interfere with the reaction. In addition, the reaction is pH dependent and should be maintained between pH 10 and pH 10.5.

The BCA method is related to the Lowry method in that protein peptide bonds first reduce cupric ion ($Cu^{2+}$) to produce a tetradentate-cuprous ion ($Cu^{1+}$) complex in an alkaline medium. The cuprous ion complex then reacts with BCA (2 molecules BCA per $Cu^{1+}$) to form an intense purple color that can be measured at 562 nm. Because BCA is stable in alkaline medium, the BCA method can be carried out in one step, compared to two steps needed in the Lowry method. The BCA method exhibits increased compatibility towards interfering compounds than the Lowry method. For example, sodium dodecyl sulfate (SDS), Triton X-100, and Tween-20 are compatible up to 5% with the BCA assay whereas compatible concentrations for SDS, Triton X-100, Tween-20 are 1%, 0.03% and 0.062%, respectively for the Lowry method. The BCA method also offers increased sensitivity and an expanded linear working range compared to the Lowry method.

The colloidal gold protein method is the most sensitive among the colorimetric protein determination methods with a sensitivity of about 2 μg/ml to 20 μg/ml. Protein binding to the colloidal gold causes a shift in its absorbance that is proportional to the amount of protein in the solution. Most common reagents, other than thiols and sodium dodecyl sulfate (SDS), are compatible with the colloidal gold protein method. The colloidal gold protein method has significant protein-to-protein variation.

The Coomassie Blue G-250 dye-binding method is based on the immediate absorbance shift of 470 nm to 595 nm that occurs when Coomassie Blue G-250 binds to protein in an acidic medium. Color development is rapid and the assay can be performed in ten minutes. The Commassie Blue G-250 dye-binding method is comparatively free from interference by common reagents except detergents, and has moderate protein-to-protein variation.

Two other dye-binding protein methods are reported using Pyrogallol Red (Watanabe et al. Clin. Chem. 32: 1551, 1988) and Pyrocatechol Violet (Fujita et al. Chem. Pharm. Bull. 32: 4161, 1984). Like the Coomassie Blue G-250 dye-binding method, both of these dye-binding protein methods exhibit variable sensitivity to various proteins (protein-to-protein variation)

A dye-binding protein assay utilizing a pyrocatechol violet-metal (PVM) complex is provided. For example, pyrocatechol violet-molybdate complex has a reddish-brown color that changes to green when deprotonated at relatively higher pH. As shown in FIG. 1, protein binding at a relatively lower pH causes the dye to deprotonate more easily by the interaction of positively charged amino acid groups stabilizing the negatively charged deprotonated dye-molybdate complex. PVM protein determination assay is rapid, sensitive and relatively free from interference by detergents, reducing agents and other common reagents, as further described. This assay has a large linear working range and low protein-to-protein variation.

In one embodiment, a protein assay reagent composition is provided. In one embodiment, the protein assay reagent composition comprises polyhydroxybenzenesulfonephthalein- or polyhydroxybenzenephthalein-type dyes such as pyrocatechol violet along with a metal. In one embodiment, the metal can be molybdenum, tungsten, bismuth, thorium, uranium, vanadium, or copper, or combinations thereof. In embodiments, the metal is present as a sodium, potassium, lithium, or ammonium salt. In one embodiment, the metal is sodium molybdate or sodium tungstate. Additional components of the composition include polyvinyl alcohol, optionally methanol, a buffer, polyvinyl pyrrolidone and at least one of a chelating agent, sodium benzoate, or α-cyclodextrin. In embodiments, the buffer can be any buffer capable of buffering in the range of about pH 1 to about pH 4. In one embodiment, the buffer is a mono- or di-aliphatic or aromatic carboxylic acid or inorganic acid. In one embodiment, the buffer is succinic acid. Other suitable buffers include phosphate, oxalic acid, phytic acid, phosphoric acid, citric acid, tricholoroacetic acid, benzoic acid, sodium acetate, sodium bisulfate, salicylic acid, hydrochloric acid, maleic acid, glycine, phthalic acid, glycylglycine and fumaric acid. Examples of suitable chelating agents include sodium oxalate, phytic acid, oxalic acid, and ethylenediaminetetraacetic acid (EDTA). Without being held to a single theory, the presence of a chelator in the protein assay reagent composition eliminates the protein determination error due to the presence of a chelating agent in the sample, e.g. urine. The presence of a chelator also may increase the color contrast of the dye.

Without being held to a single theory, polyvinyl alcohol, sodium benzoate and polyvinyl pyrrolidone may prevent protein precipitation during the assay. Other reagents which can be used to prevent protein precipitation include non-ionic surfactants such as Tween-20, Tween-80, Triton X-100, and gum arabic.

In one embodiment, the composition comprises pyrocatechol violet at a concentration from about 0.1 mM to about 0.5 mM; a metal at a concentration from about 0.05 mM to about 0.4 mM; polyvinyl alcohol at a concentration from about 0.05% w/v to about 0.4% w/v; optionally methanol at a concentration from about 0% v/v to about 10% v/v; a buffer at a concentration from about 25 mM to about 200 mM; polyvinyl pyrrolidone at a concentration from about 0.05% w/v to about 0.2% w/v; and at least one of a chelator at a concentration from about 0.05 mM to about 2 mM, or sodium benzoate at a concentration from about 1 mM to about 6 mM, wherein the pH of the protein assay reagent composition is from about pH 1 to about pH 4. In one embodiment, the metal can be molybdenum, tungsten, bismuth, thorium, uranium, vanadium, or copper, or combinations thereof. In one embodiment, the metal is molybdenum. In embodiments, the metal is present as a sodium, potassium, lithium, or ammonium salt. In one embodiment, the metal is sodium molybdate or sodium tungstate. In one embodiment, the protein assay reagent composition comprises α-cyclodextrin at a concentration from about 25 mM to about 100 mM. Without being held to a single theory, the presence of α-cyclodextrin increases the compatibility of the protein assay reagent composition to the presence of SDS.

In one embodiment, the protein assay reagent composition comprises pyrocatechol violet at a concentration of 0.26 mM; sodium molybdate at a concentration of 0.16 mM; polyvinyl alcohol at a concentration of about 0.2% w/v; methanol at a concentration of about 4%; succinic acid at a concentration of about 50 mM; sodium oxalate at a concentration of 1.0 mM; sodium benzoate at a concentration of 3.5 mM and polyvinyl pyrrolidone at a concentration of about 0.1% w/v, wherein the pH of the protein assay reagent composition is about pH 2.5.

In one embodiment, the protein assay reagent composition also comprises α-cyclodextrin at a concentration of about 50 mM.

In one embodiment, a method for determining protein concentration using the polycatechol violet-metal complex binding to protein is provided. In one embodiment, the pyrocatechol violet-metal complex is pyrocatechol violet-molybdate. The binding of the pyrocatechol violet-metal complex to protein under acidic conditions causes a shift in the absorption maximum of the dye that is measured at about 660 nm. The assay is reproducible and rapid. The assay is more linear compared to Coomasie-based Bradford assays and compatible with higher concentrations of most detergents, reducing agents, and other commonly used reagents such as chelating agents and buffers. The assay has a protein-to-protein variation of about 37%.

In one embodiment, the method comprises (a) combining the sample with the protein assay reagent composition to form a protein determination mixture; (b) incubating the protein determination mixture to result in the formation of a colored complex; (c) measuring the absorbance of the colored complex; and (d) determining the protein concentration in the sample by comparing the measured absorbance with the absorbance obtained from samples containing known concentrations of protein.

The sample for protein determination includes any solution, mixture, composition, etc. that contains or may contain protein. Examples include, but are not limited to, a biological fluid such as urine, serum, plasma, cerebrospinal fluid, cell lysates, etc. Examples also include, e.g., test solutions in conjunction with experimental or laboratory procedures.

In one embodiment, the protein assay reagent composition comprises pyrocatechol violet at a concentration from about 0.1 mM to about 0.5 mM, a metal at a concentration from about 0.05 mM to about 0.4 mM, polyvinyl alcohol at a concentration from about 0.05% w/v to about 0.4% w/v, optionally methanol at a concentration from about 0% v/v to about 10% v/v, polyvinyl pyrrolidone at a concentration from about 0.05% w/v to about 0.2% w/v and a buffer at a concentration from about 25 mM to about 200 mM. In one embodiment, the metal can be molybdenum, tungsten, bismuth, thorium, uranium, vanadium, or copper, or combinations thereof. In one embodiment, the metal is molybdenum. In embodiments, the metal is present as a sodium, potassium, lithium, or ammonium salt. In one embodiment, the metal is sodium molybdate or sodium tungstate. In one embodiment, the composition further comprises at least one of a chelating agent at a concentration from about 0.05 mM to about 2 mM or sodium benzoate at a concentration from about 1 mM to about 6 mM. In one embodiment, the composition further comprises α-cyclodextrin at a concentration from about 25 mM to about 100 mM. In one embodiment, the composition exhibits a pH from about pH 1 to about pH 4.

In one embodiment, the protein determination mixture is incubated for a time sufficient to form a colored complex. In one embodiment, the protein determination mixture is incubated for about two minutes to about twenty minutes to form a colored complex. In one embodiment, the protein determination mixture is incubated for about five minutes to form a colored complex. In one embodiment, the protein determination mixture is incubated at about 20° C. to about 25° C., e.g. room temperature, to form a colored complex.

In various embodiments, at least one of the steps of the protein determination method occurs in a test tube or a well of a multi-well plate.

In one embodiment, a kit is provided. In one embodiment, the kit comprises a protein assay reagent composition comprising pyrocatechol violet, a metal, polyvinyl alcohol, optionally methanol, polyvinyl pyrrolidone, a buffer, and at least one of a chelating agent, sodium benzoate, or α-cyclodextrin; at least one protein in a known concentration; and instructions for determining protein concentration using the kit components. In one embodiment, the metal can be molybdenum, tungsten, bismuth, thorium, uranium, vanadium, or copper, or combinations thereof. In one embodiment, the metal is molybdenum. In embodiments, the metal is present as a sodium, potassium, lithium, or ammonium salt. In one embodiment, the metal is sodium molybdate or sodium tungstate.

The following example illustrates embodiments of the method.

EXAMPLE I

Preparation of Pyrocatechol Violet-Molybdenum Complex Assay Reagent Stock

In 940 ml of ultra pure water, 5.9 g succinic acid, 0.14 g sodium oxalate and 0.5 g sodium benzoate was dissolved. Pyrocatechol violet solution (100 mg dissolved in 40 ml methanol) was added followed by the addition of 16 ml sodium molybdate solution (120 mg dissolved in 50 ml ultrapure water). The pH was adjusted to 2.5 using 50% v/v HCl solution followed by the addition of 2 g polyvinyl alcohol (30-70 kD) and 1 g polyvinyl pyrrolidone (55 kD). The solution was stirred overnight at about 20° C. to about 25° C., e.g. room temperature.

The final concentrations of the components in the Assay Reagent Stock were as follows:

50 mM succinic acid
1.0 mM sodium oxalate
3.5 mM sodium benzoate
0.26 mM pyrocatechol violet
0.16 mM sodium molybdate
4% (w/v) methanol,
0.2% (w/v) polyvinyl alcohol
0.1% (w/v) polyvinyl pyrrolidone The assay reagent can also be prepared by dissolving pyrocatechol violet in ultrapure water instead of methanol.

Spectral Analysis of the Assay Reagent

Figure 2:
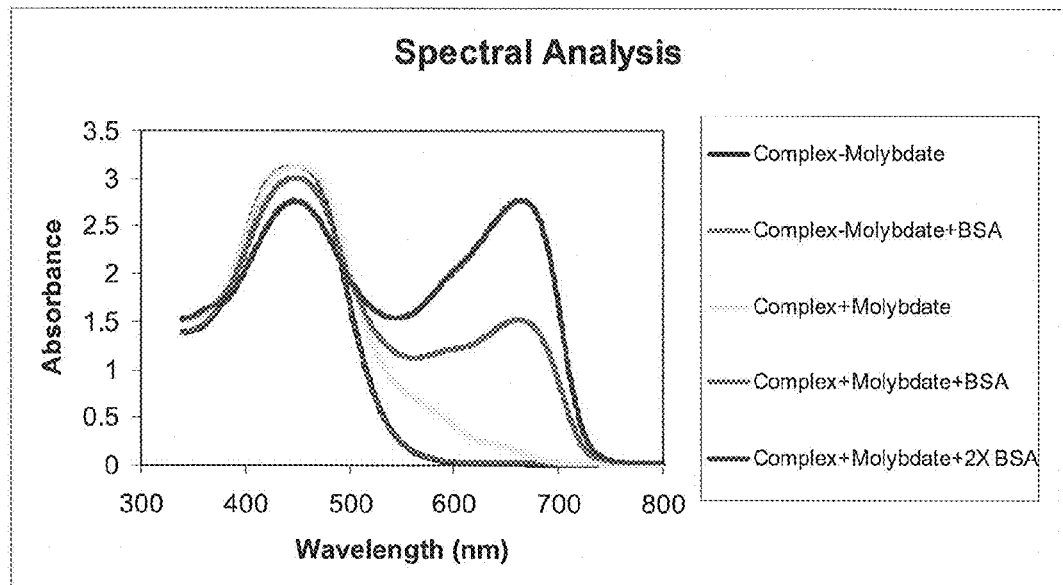
FIG. 2 shows the absorption spectra of pyrocatechol violet (PCV) in various mixtures.

Absorption spectra were recorded in a Varian Cary spectrophotometer from 340 nm-800 nm with the resultant spectra shown in FIG. 2. The concentration of bovine serum albumin (BSA) was 100 μg in the PCV+molybdate (Mo(IV))+BSA and 200 μg in the PCV+molybdate (Mo(IV))+2×BSA. The results shown in FIG. 2 showed that 660 nm was the appropriate wavelength for measuring the protein concentration.

Assay Procedure—Test Tube

Figure 3:
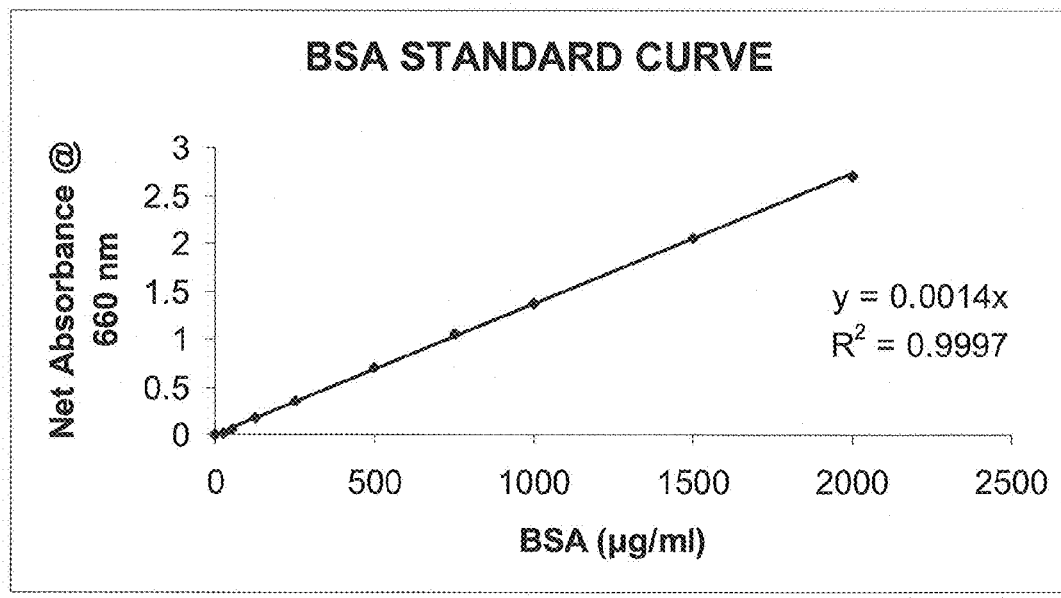
FIG. 3 shows a standard curve for quantitation of bovine serum albumin (BSA) using the PVM complex.
Figure 4:
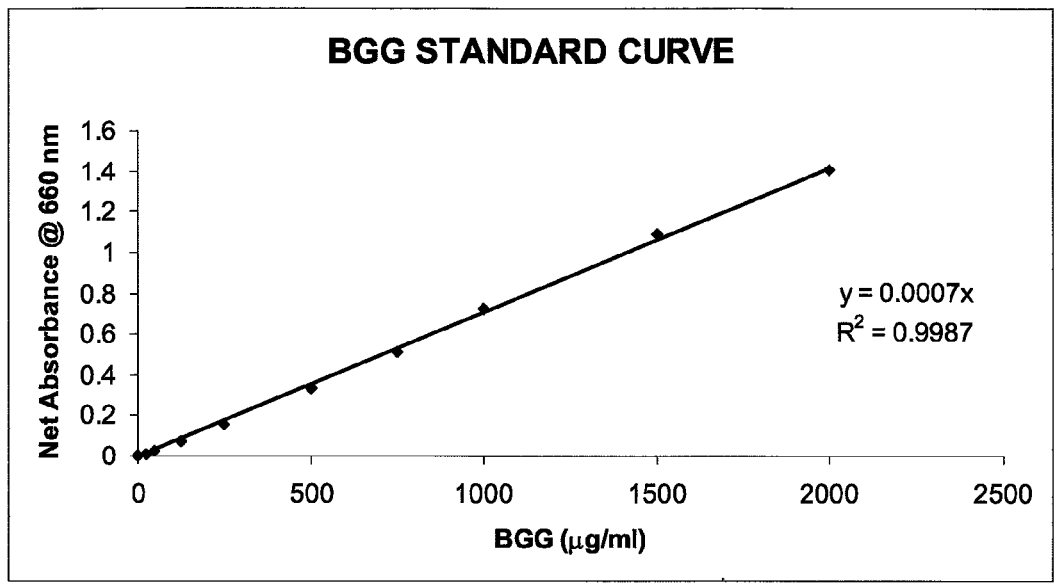
FIG. 4 shows a standard curve for quantitation of bovine gamma globulin (BGG) using the PVM complex.

To each test tube containing 0.1 ml of each BSA standard replicate (25, 50, 125, 250, 500, 750, 1000, 1500 and 2,000 μg/ml) in saline, 1.5 ml Assay Reagent solution was added, mixed well, and incubated at about 20° C. to about 25° C., e.g. room temperature, for five minutes. The absorbance of all the samples and the controls was measured. The average absorbance at 660 nm for the blank replicates (control) was subtracted from the absorbance at 660 nm for all other individual standard replicates. A standard curve, shown in FIG. 3, was generated by plotting the average blank-corrected 660 nm measurement for each standard versus its concentration in μg/ml. The results showed that the linear detection range of the assay for BSA was 25 μg/ml to 2,000 μg/ml. FIG. 4 shows the same procedure using bovine gamma globulin (BGG) and resulted in a linear detection range of the assay for BGG of 50 μg/ml to 2,000 μg/ml.

Assay Procedure—Microplate

Figure 5:
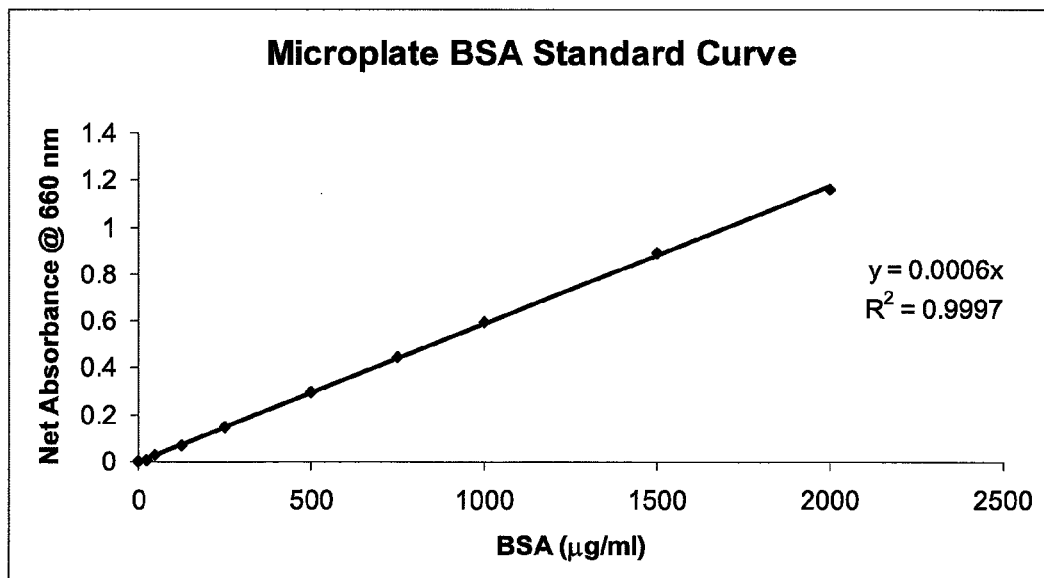
FIG. 5 shows a standard curve for quantitation of BSA using the PVM complex in a microplate procedure.
Figure 6:
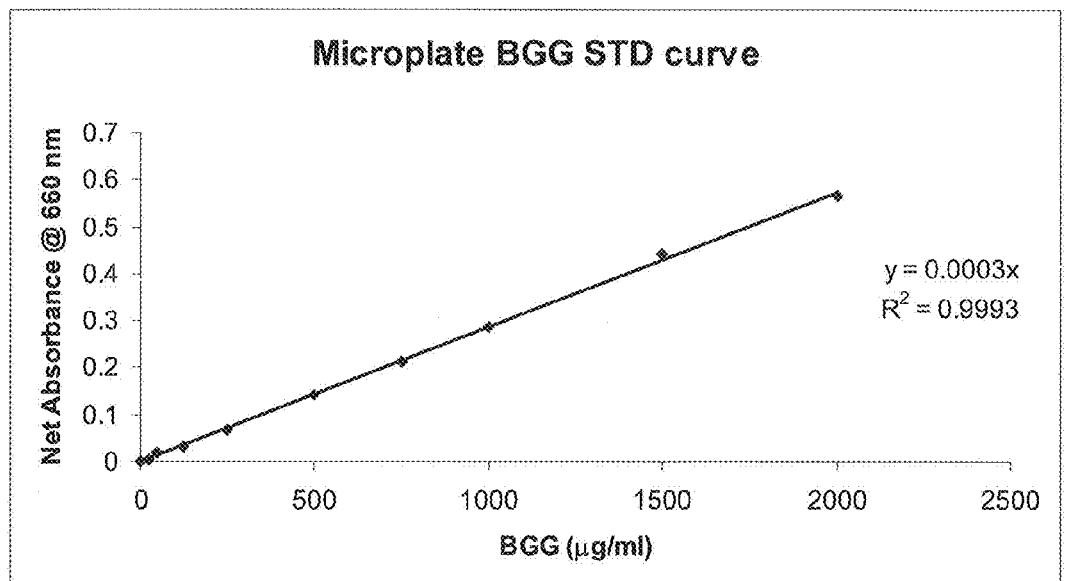
FIG. 6 shows a standard curve for quantitation of BGG using the PVM complex in a microplate procedure.

To each well containing 0.01 ml of each standard replicate of BSA (25, 50, 125, 250, 500, 750, 1000, 1500 and 2,000 μg/ml) in saline, 0.15 ml Assay Reagent solution were added. The plate was covered with sealing tape, mixed for one minute on a plate shaker, and incubated at about 20° C. to about 25° C., e.g. room temperature, for five minutes. The plate reader was set to 660 nm and using the control as a blank, the absorbance of all samples was measured. A standard curve, shown in FIG. 5, was generated by plotting the average blank-corrected 660 nm measurement for each standard versus its concentration in μg/ml. The results showed that the linear detection range of the assay for BSA was 50 μg/ml to 2,000 μg/ml. FIG. 6 shows the same procedure using bovine gamma globulin (BGG) and resulted in a linear detection range of the assay for BGG of 50 μg/ml to 2,000 μg/ml.

Compatibility of the Assay with Interfering Substances

Certain substances are known to interfere with the Coomassie-based Bradford protein assays including most ionic and non-ionic detergents, reducing agents, buffers, salts, organic solvents, etc. Substances are considered compatible in a protein determination assay if the error in protein concentration estimation of BSA at 1 mg/ml caused by the presence of the substance in the sample is less than or equal to 10%. The blank-corrected 660 nm absorbance measurements for the 1 mg/ml BSA standard+substance were compared to the net 660 nm absorbance of the 1 mg/ml BSA standard prepared in water. Maximum compatible concentrations for many substances are listed in Table 1.

TABLE 1

Compatible Substance Concentrations in the Assay

| Substances | Maximum Compatible Concentration |
|---|---|
| Detergents | |
| Polyoxyethylene (20) Sorbitan Monolaurate (Tween-20) | 10% |
| Octylphenol Ethoxylate (Triton X-114) | 0.5% |
| Octylphenol Ethoxylate (Triton X-100) | 1% |
| Octylthioglucopyranoside | 10% |
| 3-[(3-Cholamidopropyl)dimethylammonio]-1-propanesulfonate (CHAPS) | 5% |
| 3-[(3-Cholamidopropyl)dimethylammonio]-2-hydroxy-1-propanesulfonate (CHAPSO) | 4% |
| Polyglycol ether (NP-40) | 5% |
| Octyl-β-Glucoside | 5% |
| Polyoxyethyleneglycol dodecyl ether (Brij-35) | 5% |
| Sodium Dodecyl Sulfate (SDS) | 0.0125% |
| Sodium Deoxycholate | 0.25% |
| n-Tetradecyl-N,N-dimethyl-3-ammonio-1-propanesulfonate (Zwittergent 3-14) | 0.05% |
| Reducing Agents | |
| Dithiothreitol (DTT) | 500 mM |
| 2-Mercaptoethanol | 1M |
| L-Cysteine | 350 mM |
| Ascorbic acid | 500 mM |
| Tris(2-Carboxyethyl) phosphine (TCEP) | 40 mM |
| Glutathione (Reduced) | 100 mM |
| Chelating Agents | |
| ethylenediaminetetraacetic acid (EDTA) | 20 mM |
| ethylene glycol tetraacetic acid (EGTA) | 20 mM |
| Sodium Citrate | 12.5 mM |
| Buffers | |
| Phosphate-buffered Saline (PBS) | Undiluted |
| 4-(2-hydroxyethyl)-1-piperazineethanesulfonic acid (HEPES), pH 7.5 | 100 mM |
| trishydroxymethylaminomethane (Tris)-HCl, pH 8.0 | 250 mM |
| Glycine Buffer, pH 2.8 | 100 mM |
| Carbonate-Bicarbonate, pH 9.4 | 1:2 diluted |
| 2-(N-morpholino)ethane sulphonic acid (MES), pH 6.1 | 125 mM |
| 3-(N-morpholino)propane sulphonic acid (MOPS), pH 7.2 | 125 mM |
| 1,4 piperazine-bis-(ethane sulphonic acid) (PIPES), pH 6.8 | 100 mM |
| Imidazole, pH 7.0 | 200 mM |
| Borate buffer, pH 8.5 | Undiluted |
| Sodium Acetate, pH 4.8 | 100 mM |
| Miscellaneous Reagents and Solvents | |
| NaCl | 1.25M |
| guanidine hydrochloride | 2.5M |
| Urea | 8M |
| Thiourea | 2M |
| Ammonium Sulfate | 125 mM |
| Glycerol | 50% |
| NaOH | 125 mM |
| HCl | 125 mM |
| Sucrose | 50% |
| Methanol | 50% |
| Ethanol | 50% |
| DMF | 50% |
| DMSO | 50% |
| Acetone | 50% |
| Acetonitrile | 50% |
| Phenol Red | 0.5 mg/ml |
| Calcium Chloride in TBS, pH 7.2 | 40 mM |
| Cobalt Chloride in TBS, pH 7.2 | 20 mM |
| Ferric Chloride in TBS, pH 7.2 | 5 mM |
| Nickel Chloride in TBS, pH 7.2 | 10 mM |
| Zinc Chloride in TBS, pH 7.2 | 10 mM |

As shown in Table 1, the PVM method was compatible with relatively high concentrations of many detergents, reducing agents, and other commonly used reagents.

Effect of the Addition of α-Cyclodextrin on the Compatible Concentration of Sodium Dodecyl Sulfate (SDS)

As shown in Table 1, SDS at a concentration up to 0.0125% was compatible with the PVM method. The addition of 50 mM α-cyclodextrin to the assay reagent composition increased the compatible concentration of SDS up to about 5%. Addition of α-cyclodextrin also made the assay compatible with Tris-Glycine SDS sample buffer (63 mM Tris-HCl, 10% Glycerol, 2% SDS, 0.0025% bromophenol blue).

Protein-To-Protein Variability

The other commonly used total protein assay methods exhibit some degree of varying response toward proteins. These differences relate to amino acid sequence, isoelectric point, structure and the presence of certain side chains or prosthetic groups that can alter the protein's color response. Many protein assay methods use BSA or BGG as the standard against which the concentration of protein in the sample is determined. Table 2 shows typical PVM Protein Assay protein-to-protein variation. All of the proteins assayed were prepared in sets of standard concentrations ranging from 125 µg/ml to 2,000 µg/ml using the Test Tube protocol. The average response for BSA at 1 mg/ml was normalized to 1 and the average response to other proteins at 1 mg/ml was expressed as a ratio to the response with BSA. As shown in Table 2, protein-to-protein variability of the assay was moderate and acceptable.

TABLE 2

Protein-to-Protein Variation

| Protein | Ratio |
|---|---|
| Albumin, Bovine Serum | 1.00 |
| Gamma Globulin, Bovine | 0.51 |
| IgG, Human | 0.57 |
| IgG, Rabbit | 0.38 |
| IgG, Mouse | 0.48 |
| Insulin, Bovine Pancreas | 0.81 |
| Cytochrome C, Horse heart | 1.22 |
| α-Lactalbumin | 0.82 |
| Lysozyme | 0.79 |
| Myoglobin, Horse heart | 1.18 |
| Trypsin Inhibitor, Soybean | 0.38 |
| Ovalbumin | 0.54 |
| Transferrin, Human | 0.8 |
| Aldolase | 0.83 |
| Average Ratio | 0.7364 |
| Standard Deviation | 0.27253 |
| Coefficient of Variation | 37% |

Figure 7:
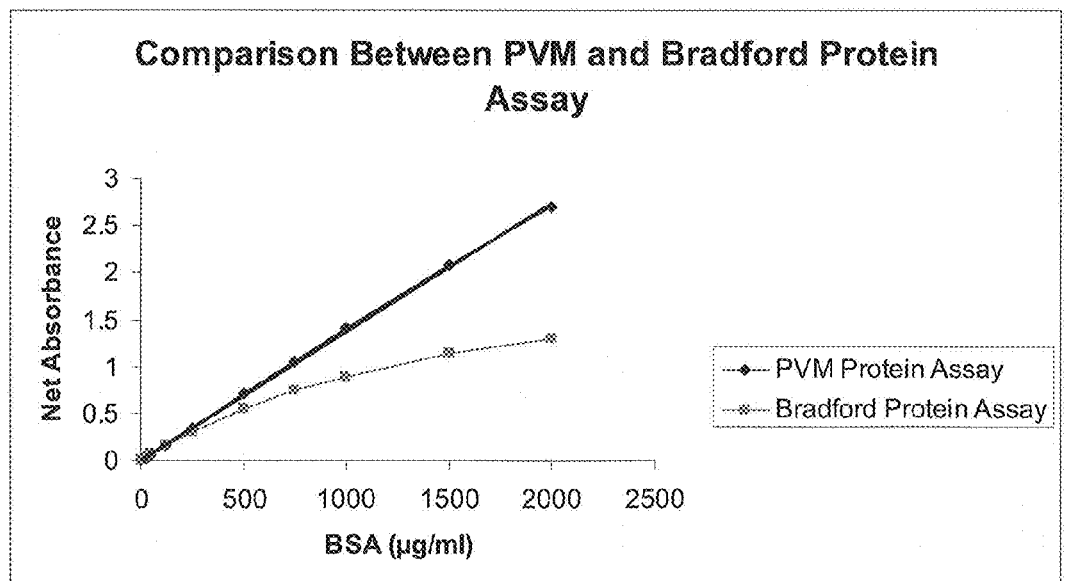
FIG. 7 compares protein determination using the PVM complex with a commercially available assay.

Comparison of Pyrocatechol Violet Molybdate Protein Assay with Coomassie-Based Bradford Protein Assay The PVM method was performed using BSA as the standard as described above for the Test Tube Protocol. The Bradford protein method used was QUICK START® (Bio-Rad, Hercules Calif.), performed according to manufacturers instructions. As shown in FIG. 7, the PVM method was more linear in the working range of 25 µg/ml to 2,000 µg/ml BSA compared to the Coomassie-based Bradford method.

Compatibility of PVM Protein Assay with Nano Drop Spectrophotometer ND-1000

To each well (96 well plate) containing 0.01 ml of each standard replicate of BSA (0, 125, 250, 500, 750, 1,000, 1,500 and 2,000 µg/ml) in saline, 0.15 ml Assay Reagent solution was added. The plate was covered with sealing tape, mixed for one minute on a plate shaker, and incubated at about 20° C. to about 25° C., e.g. room temperature, for five minutes. A blank measurement at 660 nm was obtained by loading 2 µl of the control onto the sample pedestal. Subsequently, the absorbance of all the samples was measured at 660 nm. A standard curve as shown in FIG. 8 was generated by plotting the average blank-corrected 660 nm measurement for each standard versus concentration in µg/ml.

Figure 8:
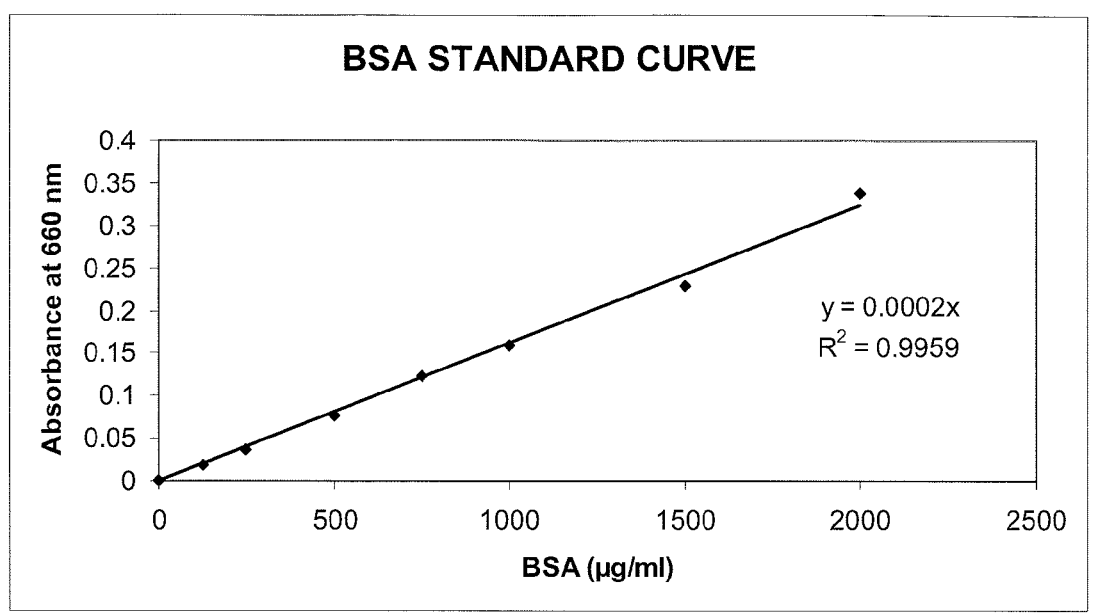
FIG. 8 shows the compatibility of a commercially available spectrophotometer with the PVM complex.

As shown in FIG. 8, PVM Protein Assay was compatible with Nano Drop's ND-1000 Spectrophotometer.

The disclosures of the references identified herein are incorporated herein in their entirety.

Other variations or embodiments will also be apparent to one of ordinary skill in the art from the above figures, description, and examples. Thus, the foregoing embodiments are not to be construed as limiting the scope of the following claims.

What is claimed is:

1. A protein assay reagent composition comprising
pyrocatechol violet at a concentration from about 0.1 mM to about 0.5 mM;
a metal at a concentration from about 0.05 mM to about 0.4 mM;
polyvinyl alcohol at a concentration from about 0.05% w/v to about 0.4% w/v;
optionally methanol at a concentration from about 0% v/v to about 10% v/v,
polyvinyl pyrrolidone at a concentration from about 0.05% w/v to about 0.2% w/v,
a buffer at a concentration from about 25 mM to about 200 mM, and
at least one of
a chelator at a concentration from about 0.05 mM to about 2 mM, or
sodium benzoate at a concentration from about 1 mM to about 6 mM,
wherein the pH of the protein assay reagent composition is from about pH 1 to about pH 4.

2. The composition of claim 1 wherein the metal is selected from the group consisting of molybdate, tungsten, bismuth, thorium, uranium, vanadium, copper, and combinations thereof.

3. The composition of claim 1 wherein the metal is present as a sodium, potassium, lithium, or ammonium salt.

4. The composition of claim 1 wherein the buffer is a mono- or di-aliphatic or aromatic carboxylic acid or an inorganic acid.

5. The composition of claim 1 wherein the chelator is selected from the group consisting of sodium oxalate, phytic acid, oxalic acid, ethylenediaminetetraacetic acid (EDTA), and combinations thereof.

6. The composition of claim 1 further comprising α-cyclodextrin at a concentration from about 25 mM to about 100 mM.

7. A protein assay reagent composition comprising
pyrocatechol violet at a concentration of 0.26 mM;
sodium molybdate at a concentration of 0.16 mM;
polyvinyl alcohol at a concentration of about 0.2% w/v;
methanol at a concentration of about 4%;
succinic acid at a concentration of about 50 mM;
sodium oxalate at a concentration of about 1.0 mM;
sodium benzoate at a concentration of 3.5 mM; and
polyvinyl pyrrolidone at a concentration of about 0.1% w/v,
wherein the pH of the protein assay reagent composition is about pH 2.5.

8. The composition of claim 7 further comprising α-cyclodextrin at a concentration of about 50 mM.

9. A method for determining protein concentration in a sample, the method comprising (a) combining the sample with a protein assay reagent composition comprising
pyrocatechol violet at a concentration from about 0.1 mM to about 0.5 mM;
a metal at a concentration from about 0.05 mM to about 0.4 mM;
polyvinyl alcohol at a concentration from about 0.05% w/v to about 0.4% w/v;
optionally methanol at a concentration from about 0% v/v to about 10% v/v,
polyvinyl pyrrolidone at a concentration from about 0.05% w/v to about 0.2% w/v,
a buffer at a concentration from about 25 mM to about 200 mM,
and at least one of
a chelator at a concentration from about 0.05 mM to about 2 mM, or
sodium benzoate at a concentration from about 1 mM to about 6 mM,
wherein the pH of the protein assay reagent composition is from about pH 1 to about pH 4, and
wherein combining the sample with the protein assay reagent composition results in a protein determination mixture;
(b) incubating the protein determination mixture for a time sufficient to form a colored complex;
(c) measuring the absorbance of the colored complex; and
(d) determining the protein concentration in the sample by comparing the measured absorbance with the absorbance obtained from at least one sample containing a known concentration of protein.

10. The method of claim 9 wherein the metal is selected from the group consisting of molybdate, tungsten, bismuth, thorium, uranium, vanadium, copper, and combinations thereof.

11. The method of claim 9 wherein the metal is present as a sodium, potassium, lithium, or ammonium salt.

12. The method of claim 9 wherein the buffer is a mono- or di-aliphatic or aromatic carboxylic acid or an inorganic acid.

13. The method of claim 9 wherein the chelator is selected from the group consisting of sodium oxalate, phytic acid, oxalic acid, and ethylenediaminetetraacetic acid (EDTA).

14. The method of claim 9 wherein the protein assay reagent composition further comprises α-cyclodextrin at a concentration from about 25 mM to about 100 mM.

15. The method of claim 9 wherein at least one of (a), (b), or (c) occurs in a test tube or a well of a multi-well plate.

16. A method to enhance compatibility of a protein determination assay with a sample containing at least one interfering substance, the method comprising (a) combining the sample with a protein assay reagent composition comprising
pyrocatechol violet at a concentration from about 0.1 mM to about 0.5 mM;
a metal at a concentration from about 0.05 mM to about 0.4 mM;
polyvinyl alcohol at a concentration from about 0.05% w/v to about 0.4% w/v;
optionally methanol at a concentration from about 0% v/v to about 10% v/v,
polyvinyl pyrrolidone at a concentration from about 0.05% w/v to about 2% w/v,
a buffer at a concentration from about 25 mM to about 200 mM,
and at least one of
a chelator at a concentration from about 0.05 mM to about 2 mM, or sodium benzoate at a concentration from about 1 mM to about 6 mM, wherein the pH of the protein assay reagent composition is from about pH 1 to about pH 4, and wherein combining the sample with the protein assay reagent composition results in a protein determination mixture;

(b) incubating the protein determination mixture for a time sufficient to result in the formation of a colored complex;

(c) measuring the absorbance of the colored complex; and (d) determining the protein concentration in the sample by comparing the measured absorbance with the absorbance obtained from at least one sample containing a known concentration of protein, wherein the interfering substance is selected from the group consisting of detergents, reducing agents, chelating agents, buffers, reagents, solvents, and combinations thereof, and wherein the method enhances the compatibility of the protein determination assay with a sample containing at least one interfering substance.

17. The method of claim 16 wherein the metal is selected from the group consisting of molybdate, tungsten, bismuth, thorium, uranium, vanadium, copper, and combinations thereof.

18. The method of claim 16 wherein the metal is present as a sodium, potassium, lithium, or ammonium salt.

19. A kit for determining protein concentration, the kit comprising a protein assay reagent composition comprising pyrocatechol violet, a metal, polyvinyl alcohol, optionally methanol, polyvinyl pyrrolidone, a buffer, and at least one of a chelator, or sodium benzoate, and instructions for determining protein concentration using the kit components.

20. The kit of claim 19 wherein the metal is selected from the group consisting of molybdate, tungsten, bismuth, thorium, uranium, vanadium, copper, and combinations thereof.

21. The kit of claim 19 wherein the metal is present as a sodium, potassium, lithium, or ammonium salt.

22. The kit of claim 19 wherein the buffer is a mono- or di-aliphatic or aromatic carboxylic acid or an inorganic acid.

23. The kit of claim 19 wherein the chelator is selected from the group consisting of sodium oxalate, phytic acid, oxalic acid, and ethylenediaminetetraacetic acid (EDTA).

24. The kit of claim 19 further comprising α-cyclodextrin, either as a component of the protein assay reagent composition or separately.

25. The method of claim 9 wherein up to about 2000 µg/ml protein is determined.

26. The method of claim 16 wherein up to about 2000 µg/ml protein is determined.

27. The method of claim 9 wherein protein precipitation in the protein determination mixture is prevented by polyvinyl alcohol and polyvinyl pyrrolidone.

28. The method of claim 16 wherein protein precipitation in the protein determination mixture is prevented by polyvinyl alcohol and polyvinyl pyrrolidone.

29. The method of claim 9 wherein the protein determination mixture is incubated for about two minutes to about twenty minutes to form a colored complex.

30. The method of claim 16 wherein the protein determination mixture is incubated for about two minutes to about twenty minutes to form a colored complex.

31. The method of claim 9 wherein the sample is a biological fluid selected from the group consisting of urine, serum, plasma, cerebrospinal fluid, and cell lysates.

32. The method of claim 16 wherein the sample is a biological fluid selected from the group consisting of urine, serum, plasma, cerebrospinal fluid, and cell lysates.

* * * * *